(12) United States Patent
Itoh

(10) Patent No.: US 6,827,021 B2
(45) Date of Patent: Dec. 7, 2004

(54) SPECIMEN CONVEYING SYSTEM

(76) Inventor: Teruaki Itoh, 5-25, Kokaihommachi, Kumamoto-shi, Kumamoto-ken (JP)

( * ) Notice: Subject to any disclaimer, the term of this patent is extended or adjusted under 35 U.S.C. 154(b) by 4 days.

(21) Appl. No.: 10/219,280

(22) Filed: Aug. 16, 2002

(65) Prior Publication Data

US 2003/0044319 A1 Mar. 6, 2003

(30) Foreign Application Priority Data

Aug. 31, 2001 (JP) ........................................ 2001-264167

(51) Int. Cl.$^7$ .............................. B61J 3/00; B65G 47/00
(52) U.S. Cl. ..................................... 104/88.01; 198/346
(58) Field of Search .......................... 104/88.01, 88.02, 104/88.03, 88.04, 96; 198/346, 465.1, 370.01

(56) References Cited

U.S. PATENT DOCUMENTS

| 3,851,593 A | * | 12/1974 | Gagnon et al. | ........... | 104/88.01 |
| 4,703,558 A | * | 11/1987 | Makinen | ...................... | 29/784 |
| 5,029,665 A | * | 7/1991 | Harada | ....................... | 180/198 |
| 6,129,026 A | * | 10/2000 | LeCroy | ................... | 104/88.01 |

FOREIGN PATENT DOCUMENTS

| JP | 57-5116 | 1/1982 |
| JP | 8-20339 | 1/1996 |
| JP | 11-292278 | 10/1999 |
| JP | P2001-118040 A | 4/2001 |

* cited by examiner

Primary Examiner—S. Joseph Morano
Assistant Examiner—Robert J. McCarry, Jr.
(74) Attorney, Agent, or Firm—Nixon & Vanderhye

(57) ABSTRACT

A specimen conveying system according to the present invention selectively supplies specimens, which are carried in by a specimen carry-in line having conveyor-belt type conveying lane, to a plurality of specimen processing lines each having a conveyor-belt type conveying lane which perform respective specific processes for the specimens. The supply of the specimens to the specimen processing lines is performed using a motor vehicle whose running is controlled by running control means including means for transmitting a command given from a host computer. The configuration of the whole system is simplified to lower the costs, and an operating passage, which crosses the conveying line, is secured to improve the efficiency of the entire specimen processing operation.

6 Claims, 3 Drawing Sheets

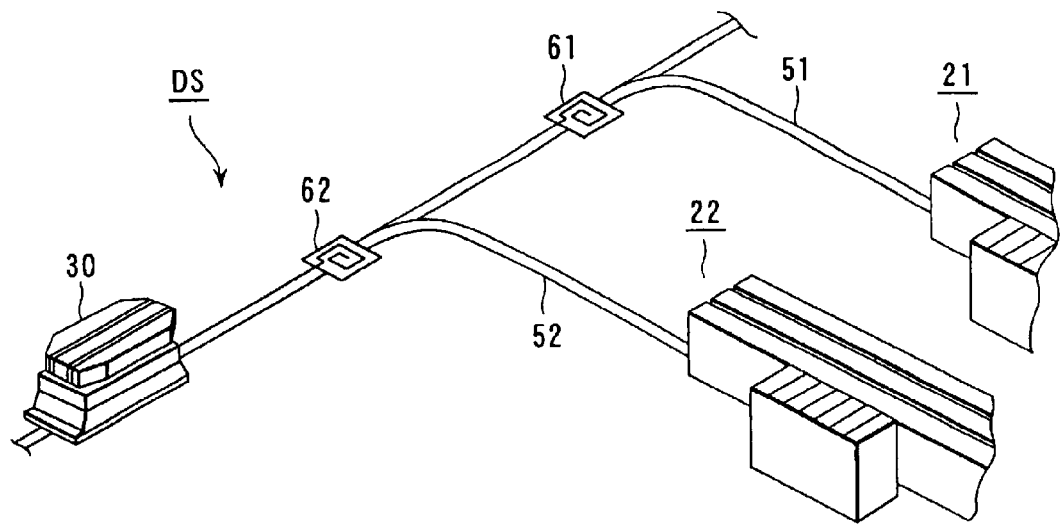
FIG. 2
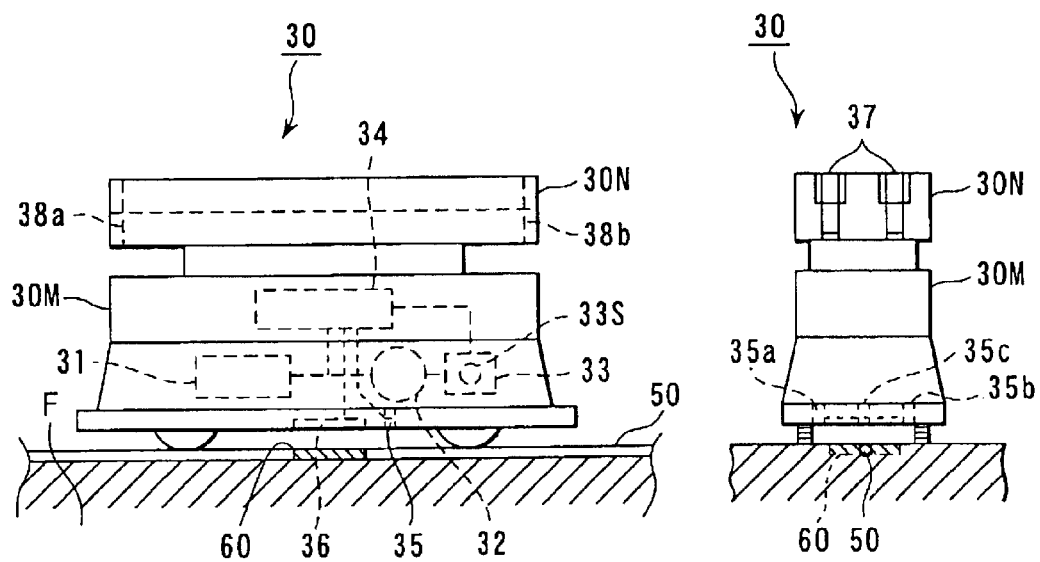
FIG. 3
FIG. 4 ent of priority from the prior Japanese Patent Application No. 2001-264167, filed Aug. 31, 2001, the entire contents of which are incorporated herein by reference.

SPECIMEN CONVEYING SYSTEM

CROSS-REFERENCE TO RELATED APPLICATIONS

This application is based upon and claims the benefit of priority from the prior Japanese Patent Application No. 2001-264167, filed Aug. 31, 2001, the entire contents of which are incorporated herein by reference.

BACKGROUND OF THE INVENTION

1. Field of the Invention

The present invention relates to a specimen conveying system for selectively supplying specimens such as blood and urine, which are carried in by a specimen carry-in line, to a plurality of specimen is processing lines to perform a specific specimen process for the specimens.

2. Description of the Related Art

A prior art specimen conveying system includes a specimen carry-in line for carrying specimens such as blood into the system and a distribution line for distributing the specimens, which are carried in by the specimen carry-in line, to a plurality of specimen processing lines. The specimen processing lines perform a specific specimen process for the specimens distributed by the distribution line. The specimen processing lines include a biochemicals line, a blood line, a coagulation line, and a urine line.

The specimen carry-in line, distribution line, and specimen processing lines each have a relatively complicated conveying mechanism with a conveyor-belt type conveying lane. In particular, the distribution line has a special direction-change mechanism for each branch point; therefore, its conveying mechanism is more complicated. The prior art specimen conveying system is very complicated in its entirety.

In the prior art specimen conveying mechanism, a conveying line is considerably long because the specimen carry-in line is connected to each of the specimen processing lines by the distribution line. An operating passage, which crosses the conveying line, is blocked, thereby causing a problem that the entire specimen processing operation is decreased in efficiency.

BRIEF SUMMARY OF THE INVENTION

An object of the present invention is to provide a specimen conveying system having the following advantages:

(a) The configuration of the whole system is simplified and the costs thereof are lowered.

(b) The operating passage that crosses the conveying line is secured and the entire specimen processing operation is improved in efficiency.

In order to attain the above object, the specimen conveying system according to the present invention has the following characteristic configuration. The other characteristic configurations will be clarified in the Detailed Description of the Invention later.

A specimen conveying system according to an aspect of the present invention selectively supplies specimens, which are carried in by a specimen carry-in line having conveyor-belt type conveying lane, to a plurality of specimen processing lines each having a conveyor-belt type conveying lane which perform respective specific processes for the specimens. The supply of the specimens to the specimen processing lines is performed using a motor vehicle whose running is controlled by running control means including a means for transmitting a command given from a host computer.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a perspective view showing part of the specimen conveying system according to the embodiment of the present invention.

FIG. 3 is a side view of a motor vehicle in the specimen conveying system according to the embodiment of the present invention.

FIG. 4 is a front view of the motor vehicle in the specimen conveying system according to the embodiment of the present invention.

DETAILED DESCRIPTION OF THE INVENTION (Embodiment)

Figure 1:
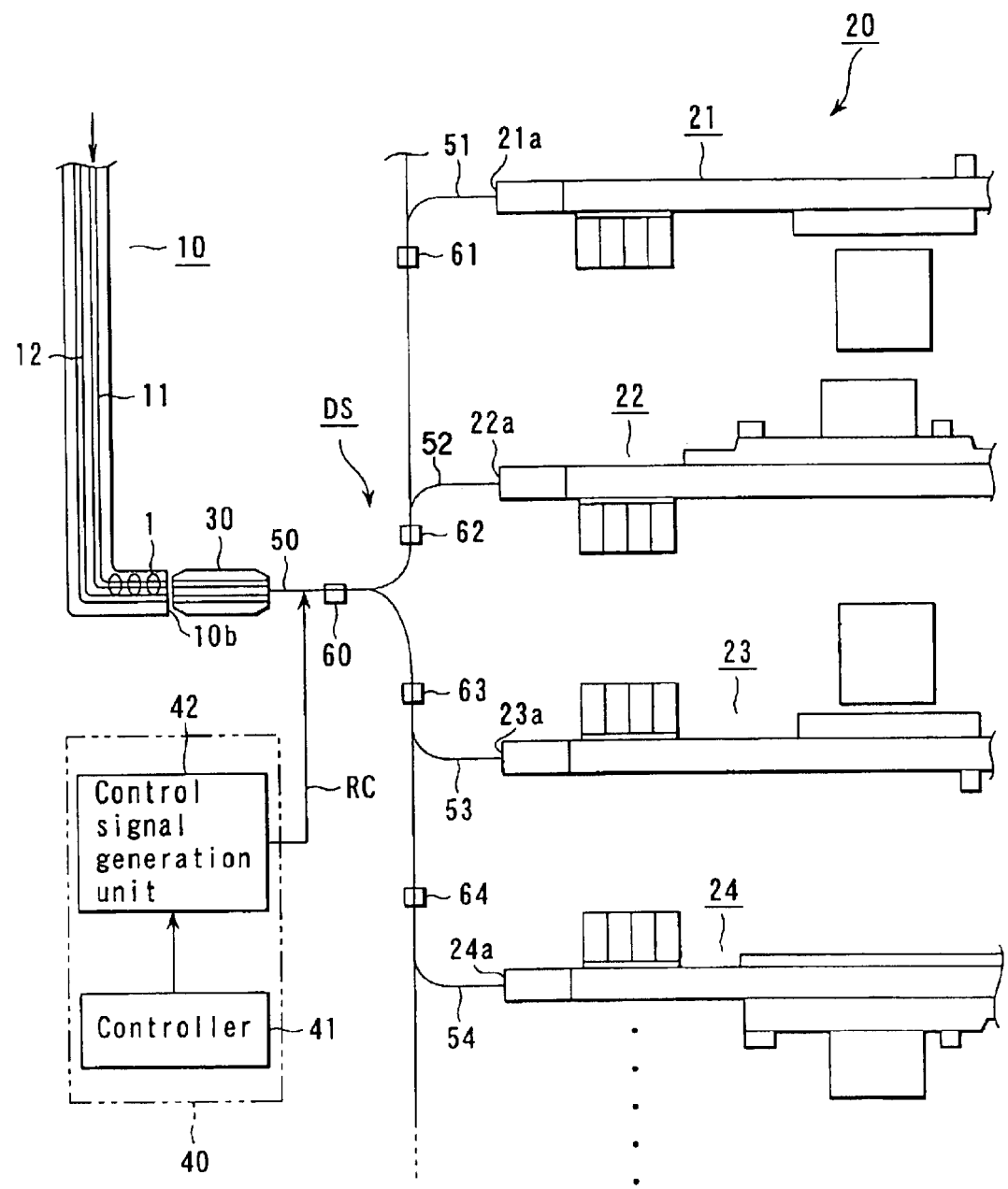
FIG. 1 is a view schematically showing a configuration of a specimen conveying system according to an embodiment of the present invention.

The specimen conveying system according to an embodiment of the present invention comprises a specimen carry-in line 10 shown at the upper left corner of FIG. 1. The specimen carry-in line 10 carries in a plurality of specimens 1, which are contained in test tubes held by a holder, through a conveyor-belt type conveying lane 11 as indicated by an arrow. In FIG. 1, reference numeral 12 denotes a conveying lane for returning the specimens.

The specimen conveying system comprises a specimen processing line group 20 including a biochemicals line 21, a blood line 22, a coagulation line 23, and a urine line 24, which are arranged in parallel to one another. These specimen processing lines 21 to 24 perform the following specific specimen process.

In the biochemicals line 21, a blood specimen contained in a blood-collecting tube is centrifuged and dispensed. The dispensed blood specimen is subjected to a given test by a biochemicals analyzer and then stored in a predetermined place.

In the blood line 22, a blood specimen contained in a blood-collecting tube is centrifuged and dispensed, as described above. The dispensed blood specimen is subjected to a given test by a blood testing analyzer and then stored in a predetermined place.

In the coagulation line 23, a blood specimen contained in a blood-collecting tube is centrifuged and dispensed, as described above. The dispensed blood specimen is subjected to a given test by a coagulation testing analyzer and then stored in a predetermined place.

In the urine line 24, a urine specimen contained in a urine-collecting tube is centrifuged and dispensed. The dispensed urine specimen is subjected to a given test by a urine testing analyzer and then stored in a predetermined place.

The specimen processing lines 21 to 24 each have the same conveyor-belt type conveying lane (not shown) as the foregoing specimen carry-in line 10.

In the specimen conveying system of the present embodiment, a distribution supply means DS using a motor vehicle 30 is adopted, as shown in FIGS. 1 and 2, in order to selectively supply the specimens 1, which are carried in by the specimen carry-in line 10, to the specimen processing lines 21 to 24.

The running of the motor vehicle 30 is controlled by a running control means RC including a command transmission means given from a host computer 40 (including a controller 41 made up of a CPU, and a control signal generation unit 42, etc.) shown in FIG. 1. Thus, the motor vehicle 30 runs along guiding conductors 50 to 54, which are formed on running routes between the specimen carry-in line 10 and the specimen processing lines 21 to 24, to receive and send the specimens 1.

Transmitting antennas 60 to 64 are provided close to the branch points of the guiding conductors 50 to 54, respectively. These antennas 60 to 64 can transmit control signals having a plurality of types of modulation frequencies (e.g., modulation frequency of the order of a megahertz), which are transmitted from the host computer 40 through the conductors at given timing, as radio waves.

The guiding conductor 50 is one formed on a common running route and the other guiding conductors 51 to 54 are ones formed on their respective branch running routes. Similarly, the transmitting antenna 60 is one provided at a branch point of the common running route and the other transmitting antennas 61 to 64 are provided at their respective branch points of the branch running routes.

As illustrated in FIGS. 3 and 4, the motor vehicle 30 is configured by a truck section 30M and a carrier section 30N mounted thereon. The truck section 30M has a driving source such that the motor vehicle 30 can run on, e.g., the guiding conductor 50 formed on a floor surface F. The driving source includes a motor 32 rotated by electric energy from a battery 31, a power transmission mechanism 33 having at least a steering mechanism 33S and a deceleration mechanism, and a controller 34. The motor vehicle 30 includes a photosensor 35 (35a, 35b, 35c), which is one of components of automatic follow-up control means, in such a manner that the truck section 30M can automatically follow the guiding conductors 50 to 54. The motor vehicle 30 also includes a receiving antenna 36 on the bottom of the truck section 30M. The receiving antenna 36 can receive the radio waves from the transmitting antennas 60 to 64.

When the steering mechanism 33S receives a signal having a specific modulation frequency that is assigned to the motor vehicle 30 via the receiving antenna 36, it steers the truck section 30M in a designated direction at a branch point, which is located close to a position in which the mechanism 33S receives the signal.

The front and rear portions of each of the truck section 30M and carrier section 30N of the motor vehicle 30 are formed into the same shape. The front portion (left end of FIG. 3) of the carrier section 30N has a first coupling section 38a that can be coupled to one end of the specimen carry-in line 10, and the rear portion (right end of FIG. 3) thereof has a second coupling section 38b that can be coupled to one end of each of the specimen processing lines 21 to 24. Further, a conveying lane 37 that can receive and send the specimens 1 is formed on the top of the carrier section 30N. One end of the conveying lane 37 can be connected to an output end 10b of the specimen carry-in line 10. The other end of the conveying lane 37 can selectively be connected to input ends 21a to 24a of the specimen processing lines 21 to 24.

Figure 5:
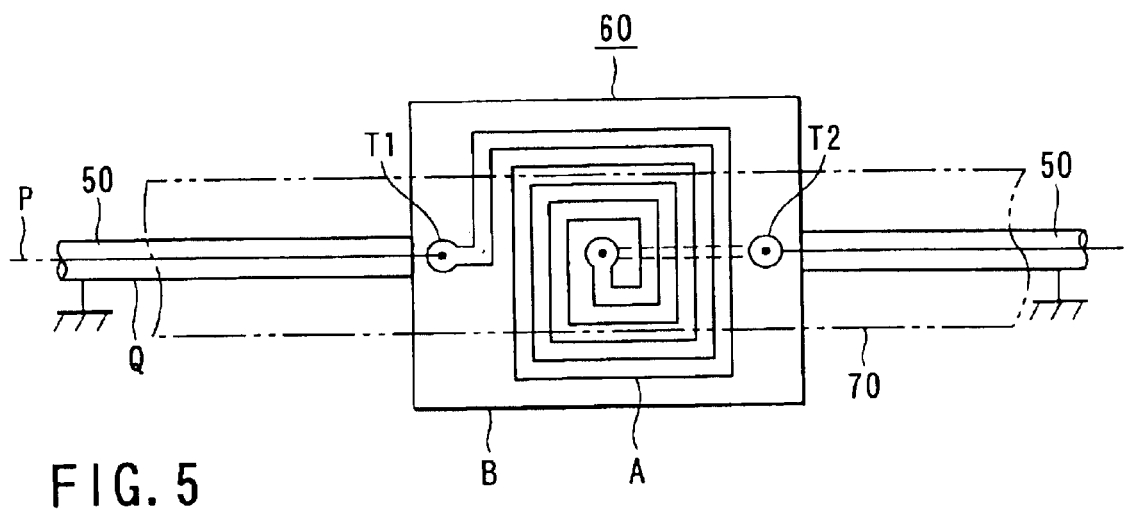
FIG. 5 is a plan view of a guiding conductor and a transmitting antenna in the specimen conveying system according to the embodiment of the present invention.

As shown in FIG. 5, the guiding conductor 50 is made of a coaxial cable including a center conductor P and an external conductor Q that are formed coaxially with each other. The transmitting antenna 60 is a planar antenna formed on an insulation substrate B, and the planar antenna has a spiral antenna element A that is made of a thin-film conductor. In FIG. 5, a broken line 70 shows a running route marking belt made of, e.g., a black tape that covers the running routes on which the guiding conductor 50 and transmitting antenna 60 are formed such that the motor vehicle 30 can easily follow the running routes. However, the running route marking belt 70 need not always be provided but can be removed.

Figure 6A:
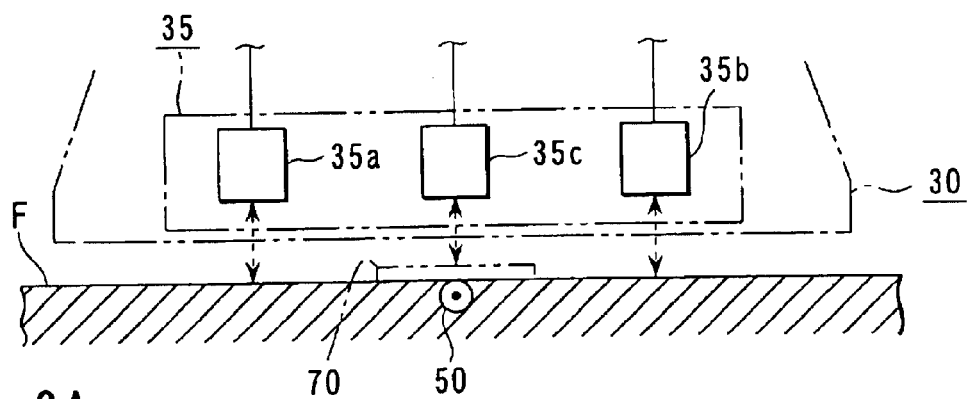
FIG. 6A is a view showing a control operation performed by an automatic follow-up control means in the specimen conveying system according to the embodiment of the present invention.
Figure 6B:
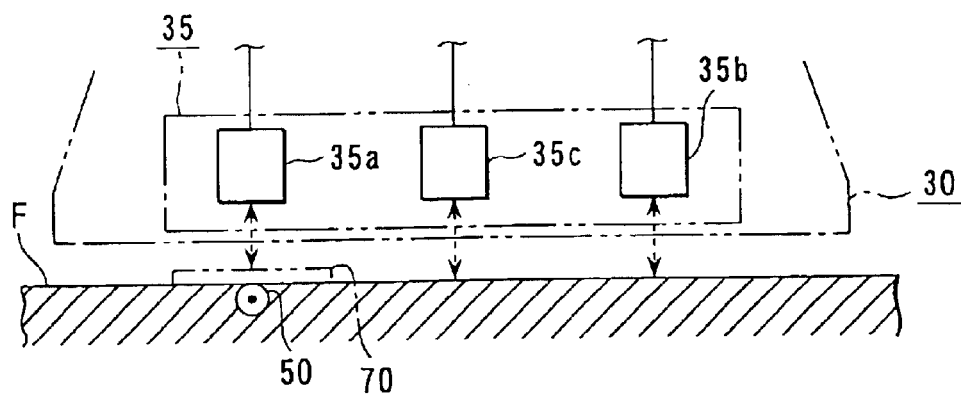
FIG. 6B is a view showing another control operation performed by the automatic follow-up control in the specimen conveying system according to the embodiment of the present invention.

As shown in FIGS. 6A and 6B, the photosensor 35 includes photosensors 35a and 35b located on both sides of the motor vehicle 30 and a photosensor 35c located in the center thereof.

When the photosensor 35c catches the running route marking belt 70 covering the guiding conductor 50 as shown in FIG. 6A, the motor vehicle 30 runs in a straight line without correcting its route. When the motor vehicle 30 shifts to the right and the left-hand photosensor 35a detects the running route marking belt 70 as shown in FIG. 6B, the automatic follow-up control means operates to move the steering mechanism 33S in a given direction. As a result, the route of the motor vehicle 30 is corrected such that it returns to the original position. Though not shown, when the motor vehicle 30 shifts to the left and the right-hand photosensor 35b detects the belt 70, the automatic follow-up control means operates to move the steering mechanism 33S in a direction opposite to the above direction. As a result, the route of the motor vehicle 30 is corrected such that it returns to the original position.

In the foregoing specimen conveying system according to the present embodiment, the specimens 1 carried in by the specimen carry-in line 10 are selectively sent to a designated one of the specimen processing lines 21 to 24 by the motor vehicle 30 whose running is controlled by the running control means RC. The motor vehicle 30 runs to automatically follow the guiding conductors 50 to 54 by the automatic follow-up control means 34 and 35. If the motor vehicle 30 acquires a signal having a specific modulation frequency, which is assigned to the motor vehicle 30 itself, at a specific branch point, it turns to a given direction at the branch point and exactly arrives at a given specimen processing line. Thus, even though a plurality of motor vehicles 30 run at the same time, they can exactly be guided to their respective specimen processing lines 21 to 24 without any trouble.

Since the effective range of radio waves emitted from the transmitting antennas 60 to 64 is at most 10 cm, there is no fear that the radio waves interfere with each other. Since, moreover, a coaxial cable formed by a center conductor P and an external conductor Q shielding the center conductor P is used, extraneous noises can be block out.

(Features of the Embodiment)

[1] A specimen conveying system according to the above embodiment, comprises:

a specimen carry-in line 10 which carries in specimens 1 through conveyor-belt type conveying lanes 11 and 12;

a plurality of specimen processing lines 21, 22, . . . each having a conveyor-belt type conveying lane, which perform respective specific processes for the specimens 1 carried in by the specimen carry-in line 10; and distribution supply means DS for selectively distributing and supplying the specimens 1 carried in by the specimen carry-in line 10 to the plurality of specimen processing lines 21, 21, wherein the distribution supply means DS supplies the specimens 1 received at an output end 10b of the specimen carry-in line 10 to a specific one (e.g., 21) of the plurality of specimen processing lines 21, 22, . . . by a motor vehicle 30 whose running is controlled by running control means RC including means for transmitting a command given from a host computer 40.

In the above-described specimen conveying system, the specimens 1 carried in by the specimen carry-in line 10 are selectively supplied to the specimen processing lines 21, 22, . . . by the motor vehicle 30. Unlike in the prior art, therefore, a distribution line including a conveyor-belt type conveying lane having a complicated direction-change mechanism need not be formed between the specimen carry-in line 10 and the plurality of specimen processing lines 21, 22, . . . ; thus, the configuration of the whole conveying system can be simplified and the costs thereof can be lowered. Since, furthermore, no distribution line is formed between them, a relatively long line is divided. Consequently, an operating passage, which crosses the conveying line, is secured and accordingly the efficiency of the whole specimen processing operation can be improved.

[2] In the specimen conveying system according to the above paragraph [1], the running control means RC includes:

guiding conductors 50, 51, . . . , which are formed along running routes between the specimen carry-in line 10 and the plurality of specimen processing lines 21, 22, . . . ; and transmitting antennas 60, 61 . . . provided close to branch points of the guiding conductors 50, 51, . . . , which transmit control signals having a plurality of types of modulation frequencies, which are transmitted from the host computer 40 through the guiding conductors 50, 51, . . . , as radio waves, and the motor vehicle 30 includes:

a truck section 30M having a driving source (32, 33 and 34) such that the motor vehicle can run by itself;

automatic follow-up control means (34, 35) provided such that the truck section 30M can automatically follow the guiding conductors 50, 51, . . . ;

a receiving antenna 36 provided in the truck section 30M so as to receive the radio waves from the transmitting antennas 60, 61, . . . ; and a steering mechanism 33S that receives a control signal having a specific modulation frequency that is assigned to the motor vehicle 30 through the receiving antenna 36 and steers the truck section 30M in a designated direction at a branch point which is located in a position where the control signal is received.

The specimen conveying system produces the same advantages as those of the system described in above paragraph [1]. When the motor vehicle 30 receives a signal having a specific modulation frequency assigned to the motor vehicle 30 at a branch point, it steers the truck section 30M in a designated direction at the branch point. Even though a plurality of motor vehicles 30 run at the same time, they can exactly be guided to a given one of the specimen processing lines (one of 21, 22, 23, 24 . . . ) without any trouble.

[3] In the specimen conveying system according to the above paragraph [2], the guiding conductors 50, 51, . . . are coaxial cables.

The specimen conveying system produces the same advantages as those of the system described in above paragraph [2]. Extraneous noises can be almost block out by the shielding effect of the coaxial cables.

[4] In the specimen conveying system according to the above paragraph [2], at least the transmitting antennas 60, 61, . . . of the transmitting and receiving antennas are planar antennas obtained by forming a spiral antenna element A, which is made of a thin-film conductor, on an insulation substrate B.

The specimen conveying system produces the same advantages as those of the system described in above paragraph [2]. Since the transmitting antennas 60, 61, . . . can be provided without greatly projecting from the floor surface F, they do not obstruct the running of the motor vehicle 30.

[5] In the specimen conveying system according to the above paragraphs [1] to [4], the motor vehicle 30 has a first coupling section 38a at the front, a second coupling section 38b at the rear, and a conveying lane at the top, the first coupling section 38a being coupled to one end of the specimen carry-in line 10, the second coupling section 38b being coupled to one end of each of the specimen processing lines 21, 22, . . . , and the conveying lane 37 being selectively connected to the output end 10b of the specimen carry-in line 10 or each of input ends 21a, 22a, . . . of the plurality of specimen processing lines 21, 22, . . . and receiving and sending the specimens 1.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A specimen conveying system comprising:

a specimen carry-in line which carries in specimens through conveying lanes;

specimen processing lines each having a conveying lane, which perform respective processes for the specimens carried in by the specimen carry-in line; and distribution supply means for selectively distributing and supplying the specimens carried in by the specimen carry-in line to the specimen processing lines, wherein the distribution supply means supplies the specimens received at an output end of the specimen carry-in line to one of the specimen processing lines by a vehicle whose running is controlled by running control means including means which transmits a command supplied from a host computer, the running control means comprising:

guiding conductors formed along running routes between the specimen carry-in line and the specimen processing lines; and transmitting antennas provided close to branch points of the guiding conductors, for transmitting control signals transmitted from the host computer through the guiding conductors as radio waves having modulation frequencies; and the vehicle comprising:

a truck section having a driving source such that the vehicle runs by itself;

automatic follow-up control means enabling the truck section to automatically follow the guiding conductors;

a receiving antenna provided in the truck section for receiving radio waves from the transmitting antennas; and a steering mechanism for receiving a control signal having a specific modulation frequency assigned to the vehicle through the receiving antenna and steering the truck section in a designated direction at a branch point located in a position where the control signal is received.

2. The specimen conveying system according to claim 1 wherein the guiding conductors are coaxial cables.

3. The specimen conveying system according to claim 1, wherein at least the transmitting antennas of the transmitting and receiving antennas are planar antennas obtained by forming a spiral antenna element, made of a thin-film conductor and positioned on an insulation substrate.

4. The specimen conveying system according to claim 1, wherein the vehicle has a first coupling section at a front portion thereof, a second coupling section at a rear portion thereof, and a conveying lane at a top portion thereof, the first coupling section being coupled to one end of the specimen carry-in line, the second coupling section being coupled to one end of each of the specimen processing lines, and the conveying lane being selectively connected to the output end of the specimen carry-in line or each of input ends of the plurality of specimen processing lines for receiving and sending the specimens.

5. The specimen conveying system according to claim 2, wherein the vehicle has a first coupling section at a front portion thereof, a second coupling section at a rear portion thereof, and a conveying lane at a top portion thereof, the first coupling section being coupled to one end of the specimen carry-in line, the second coupling section being coupled to one end of each of the specimen processing lines, and the conveying lane being selectively connected to the output end of the specimen carry-in line or each of input ends of the plurality of specimen processing lines for receiving and sending the specimens.

6. The specimen conveying system according to claim 3, wherein the vehicle has a first coupling section at a front portion thereof, a second coupling section at a rear portion thereof, and a conveying lane at a top portion thereof, the first coupling section being coupled to one end of the specimen carry-in line, the second coupling section being coupled to one end of each of the specimen processing lines, and the conveying lane being selectively connected to the output end of the specimen carry-in line or each of input ends of the plurality of specimen processing lines and receiving for sending the specimens.

* * * * *